US010191022B2

(12) United States Patent
Hinnrichs

(10) Patent No.: US 10,191,022 B2
(45) Date of Patent: Jan. 29, 2019

(54) GAS IMAGER EMPLOYING AN ARRAY IMAGER PIXELS WITH ORDER FILTERS

(71) Applicant: Michele Hinnrichs, Solvang, CA (US)

(72) Inventor: Michele Hinnrichs, Solvang, CA (US)

(73) Assignee: UVIA GROUP LLC, Humacao, PR (US)

( * ) Notice: Subject to any disclaimer, the term of this patent is extended or adjusted under 35 U.S.C. 154(b) by 96 days.

(21) Appl. No.: 15/242,231

(22) Filed: Aug. 19, 2016

(65) Prior Publication Data
US 2016/0356702 A1  Dec. 8, 2016

Related U.S. Application Data

(63) Continuation-in-part of application No. 14/211,206, filed on Mar. 14, 2014, now abandoned.

(60) Provisional application No. 61/789,208, filed on Mar. 15, 2013.

(51) Int. Cl.
| | | |
|---|---|---|
| G01N 33/00 | (2006.01) | |
| G01J 3/18 | (2006.01) | |
| G02B 5/18 | (2006.01) | |
| G01J 3/02 | (2006.01) | |
| G01N 21/3504 | (2014.01) | |
| G01J 3/26 | (2006.01) | |
| G01J 3/28 | (2006.01) | |
| G01J 1/06 | (2006.01) | |

(52) U.S. Cl.
CPC .......... *G01N 33/0027* (2013.01); *G01J 3/027* (2013.01); *G01J 3/0208* (2013.01); *G01J 3/0224* (2013.01); *G01J 3/0229* (2013.01); *G01J 3/18* (2013.01); *G01J 3/26* (2013.01); *G01N 21/3504* (2013.01); *G02B 5/1885* (2013.01); *G01J 1/06* (2013.01); *G01J 2003/1828* (2013.01); *G01J 2003/2806* (2013.01); *G01J 2003/2826* (2013.01); *G01N 2021/3513* (2013.01)

(58) Field of Classification Search
CPC ... G01N 21/31; G01N 33/0027; G01J 3/0229; G01J 3/18; G01J 3/447; G01J 2003/1828; G01J 2003/2826; G02B 5/1885
USPC ........................................................ 359/566
See application file for complete search history.

(56) References Cited

U.S. PATENT DOCUMENTS

| | | | | |
|---|---|---|---|---|
| 2006/0209413 | A1* | 9/2006 | Kim | B82Y 20/00 359/577 |
| 2009/0321645 | A1* | 12/2009 | Hinnrichs | G01J 5/061 250/338.5 |
| 2013/0229658 | A1* | 9/2013 | Jouanique-Dubuis | G01J 3/0289 356/437 |

\* cited by examiner

*Primary Examiner* — Wen Huang
(74) *Attorney, Agent, or Firm* — Felix L. Fischer

(57) ABSTRACT

A spectral radiation gas detector has at least one lenslet with a circular blazed grating for diffraction of radiation to a focal plane. A detector is located at the focal plane receiving radiation passing through the at least one lenslet for detection at a predetermined diffraction order. A plurality of order filters are associated with the at least one lenslet to pass radiation at wavelengths corresponding to the predetermined diffraction order, each filter blocking a selected set of higher orders. A controller is adapted to compare intensity at pixels in the detector associated with each of the plurality of order filters and further adapted to determine a change in intensity exceeding a threshold.

5 Claims, 20 Drawing Sheets

GAS IMAGER EMPLOYING AN ARRAY IMAGER PIXELS WITH ORDER FILTERS

REFERENCE TO RELATED APPLICATIONS

This application is a continuation in part of application Ser. No. 14/211,206 filed on Mar. 14, 2014 entitled LENSLET ARRAY WITH INTEGRAL TUNED OPTICAL BANDPASS FILTER AND POLARIZATION which claims priority of U.S. provisional application Ser. No. 61/789,208 filed on Mar. 15, 2013 the disclosure of which is incorporated herein by referenced.

BACKGROUND

Field

This invention relates generally to the field of diffractive lenslet optics for spectral imaging and more particularly to an image array employing order filters associated with pixels or pixel groups in an image array for enhanced detection of higher order wavelengths and a controller for gas detection based on relative intensity of radiation passed by the order filters.

Description of the Related Art

Spectral imaging may be accomplished using circular blazed grating diffractive lenslet arrays to discriminate various wavelengths. The preparation of diffractive lenslets for radiation, such as radiation in the visible and infrared bands, requires precision grinding to provide appropriate blazing. Additional precision in discrimination of properties of the incoming radiation to a detector for depth measurement in a substance or other characteristics is also desired. Spectral imaging may be employed for remote sensing and gas detection.

It is desirable to provide a spectral imaging system which reduces the precision required for blazing of lenslets or conversely enhances detection at a given precision and provides discrimination capability for gas detection.

SUMMARY

The embodiments disclosed herein overcome the shortcomings of the prior art by providing a spectral radiation gas detector having at least one lenslet with a circular blazed grating for diffraction of radiation to a focal plane. A detector is located at the focal plane of the lenslet receiving radiation passing through the at least one lenslet for detection at a predetermined diffraction order. A plurality of order filters are associated with the at least one lenslet to pass radiation at wavelengths corresponding to the predetermined diffraction order, each filter blocking a selected set of higher orders. A controller is adapted to compare intensity at pixels in the detector associated with each of the plurality of order filters and further adapted to determine a change in intensity exceeding a threshold.

Implemented in a first embodiment, the spectral radiation gas detector includes an array of lenslets for a set of wavelengths that receives in-band radiation, each lenslet having a circular blazed grating for diffraction of an associated wavelength from the set at the focal plane. A detector at the focal plane receives radiation passing through the array of lenslets for detection of wavelengths at a predetermined order in the bandpass of interest. An array of order filters equal in number to the array of lenslets is provided. Each order filter in the array is associated with a lenslet of the array and positioned in the optical path of the detector to pass radiation at wavelengths corresponding to the predetermined order in the bandpass of interest Implemented in a second embodiment, one lens provides in-band radiation to a repeating array of order filters, each filter in the array associated with a pixel in the detector at the focal plane detector to pass radiation at wavelengths corresponding to the predetermined order in the bandpass of interest.

These and other features and advantages of the present invention will be better understood by reference to the following detailed description of exemplary embodiments when considered in connection with the accompanying drawings.

DETAILED DESCRIPTION

Figure 1:
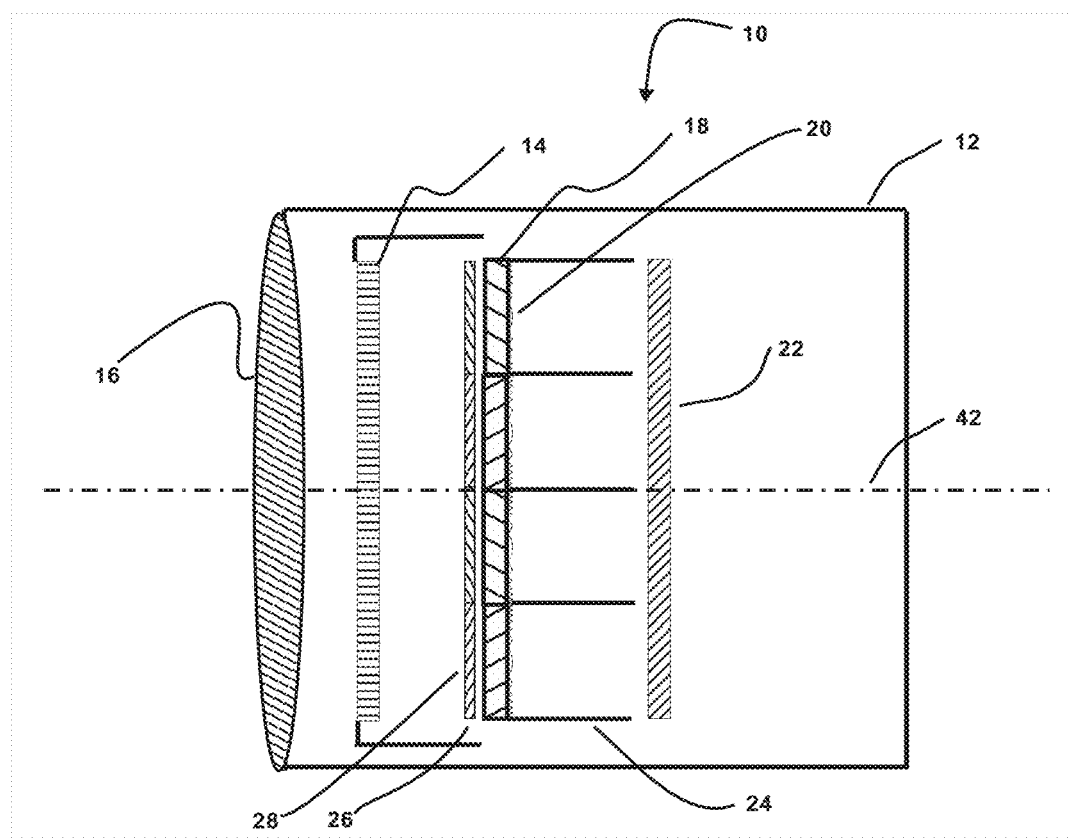
FIG. 1 is a schematic side view of a spectral radiation detector employing a first embodiment.

Embodiments shown in the drawings and described herein provide a lenslet array in which each lenslet is designed for diffraction of a predetermined wavelength of radiation at a desired focal length. A focal plane array (FPA) as a detector receives radiation transmitted through the lenslet array for detection of radiation wavelengths selected by diffraction order from each lenslet. A diffraction order filter is employed to segregate higher and/or lower order diffracted wavelengths and pass only the selected diffraction order to the FPA. Further discrimination of the incoming radiation is accomplished by providing in the array multiple lenslets for each desired wavelength and associating a polarization filter of desired orientation with each of the same wavelength lenslets.

Referring to the drawings, FIG. 1 shows an example spectral radiation detector 10 having a Dewar enclosure 12 with a window 14. A collimating lens 16 provides collimated radiation to a diffraction array 18 having circular blazed grating lenslets 20 for N wavelengths, to be described in greater detail subsequently. A FPA 22 receives radiation from the diffraction array 18 with light baffles 24 incorporated intermediate the array and FPA for segregation of radiation from the individual lenslets 20. An order filter 26 is associated with the lenslet array in the optical path between the collimating lens 16 and FPA 22. For the example embodiment the order filter 25 is mounted between the collimating lens 16 and diffraction array 18. Order filter 26 comprises an array of separate filter elements 28 associate with each lenslet 20 in the lenslet array 18

Figure 2:
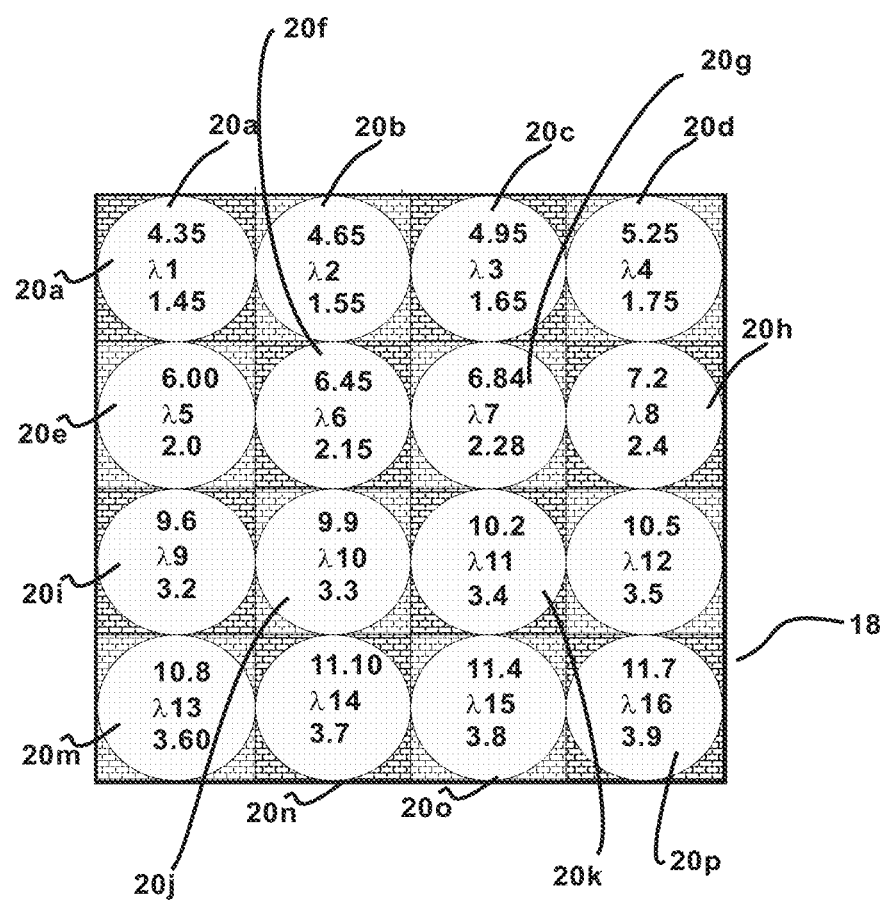
FIG. 2 is a detailed front view of the lenslet array employed in the spectral radiation detector.

An example lenslet array 18 is shown in FIG. 2 with 16 individual lenslets 20a-20p. Each lenslet is blazed to provide radiation to the focal plane at the FPA for a wavelength, $\lambda$ and a higher order, for a second wavelength, $\lambda'$. For an exemplary embodiment described in detail herein $3^{rd}$ order is employed as the selected higher order. For example, lenslet 20a provides $1^{st}$ order diffraction for $\lambda_1$ of 4.35 microns and $3^{rd}$ order diffraction of $\lambda_1'$ at 1.45 microns. Filter 26 is employed to pass radiation wavelengths closely surrounding the $3^{rd}$ order wavelengths for each of the lenslets thereby providing the FPA with radiation having high sensitivity because the other order radiation is filtered out, as will be described in greater detail subsequently. For an example embodiment as shown in FIG. 2 for the lenslet array 18, a unique order filter for each lenslet is employed to keep both higher and lower order of diffracted radiation from leaking through thereby allowing detection of a selected order or spectral bandwidth ($3^{rd}$ order in the example) which may have better properties for detection by the FPA than the $1^{st}$ order wavelength passed by the diffracting lens. For this example 16 different bandpass order filters to filter out 90% of higher and lower orders of light for each of the 16 elements in the 4×4 lenslet array with each of the lenslets designed at $1^{st}$ order but used at $3^{rd}$ order is shown. The $1^{st}$ order design wavelength, $3^{rd}$ order detection wavelength and the bandpass characteristics of individual filter elements 28 of the order filter 26 are shows in Table 1 below. The embodiment described employs a bandpass filter while alternative embodiments may employ single or paired high pass or low pass filters or single or paired notch filters for wavelengths adjacent the detection wavelength as may be desirable for greatest efficiency in detecting the desired order wavelength at the focal plane of the spectral radiation detector.

TABLE 1

| Lenslet | Design Wavelength $1^{st}$ order $\lambda$ | Used for Detection Wavelength $3^{rd}$ order $\lambda'$ | Filter element | Order Bandpass Filter Low cutoff | High cutoff | Bandpass |
|---|---|---|---|---|---|---|
| 20p | 11.7 | 3.9 | 28p | 3.60 | 4.26 | 0.66 |
| 20o | 11.4 | 3.8 | 28o | 3.50 | 4.15 | 0.65 |
| 20n | 11.1 | 3.7 | 28n | 3.41 | 4.04 | 0.63 |
| 20m | 10.8 | 3.6 | 28m | 3.32 | 3.93 | 0.61 |
| 20l | 10.5 | 3.5 | 28l | 3.23 | 3.82 | 0.59 |
| 20k | 10.2 | 3.4 | 28k | 3.13 | 3.71 | 0.58 |
| 20j | 9.9 | 3.3 | 28j | 3.04 | 3.60 | 0.56 |
| 20i | 9.6 | 3.2 | 28i | 2.95 | 3.50 | 0.55 |
| 20h | 7.2 | 2.4 | 28h | 2.21 | 2.62 | 0.41 |
| 20g | 6.84 | 2.28 | 28g | 2.10 | 2.50 | 0.40 |
| 20f | 6.45 | 2.15 | 28f | 1.98 | 2.35 | 0.37 |
| 20e | 6.00 | 2.00 | 28e | 1.84 | 2.19 | 0.35 |
| 20d | 5.25 | 1.75 | 28d | 1.61 | 1.91 | 0.30 |
| 20c | 4.95 | 1.65 | 28c | 1.52 | 1.80 | 0.28 |
| 20b | 4.65 | 1.55 | 28b | 1.43 | 1.70 | 0.27 |
| 20a | 4.35 | 1.45 | 28a | 1.33 | 1.59 | 0.26 |

Figure 3:
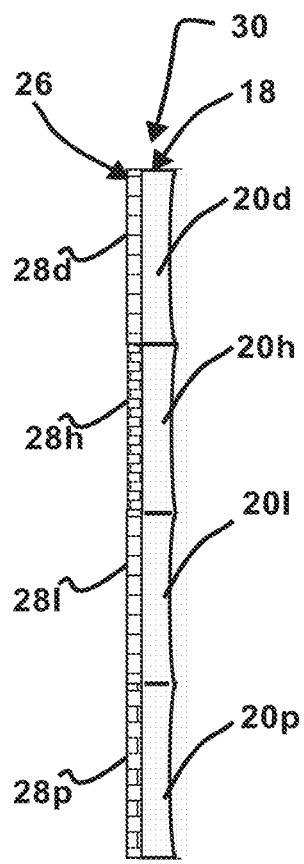
FIG. 3 is a side view of the lenslet array with an integral thin film order filter array integrated on the same substrate.
Figure 4:
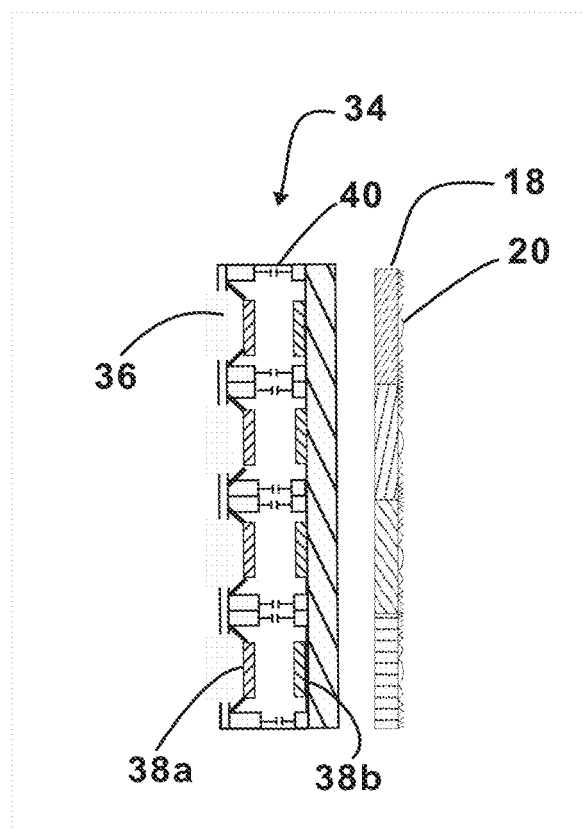
FIG. 4 is a side view of the lenslet array with a Fabry-Perot filter as the order filter mounted in front of the lenslet array.

Filter 26 may be accommodated in various forms for the embodiments herein. The order filter 26 may be placed on a separate substrate placed between the collimating lens and the lenslet array as shown in FIG. 1 or between the lenslet array and the focal plane array. As shown in FIG. 3, order filter 26 may be embodied in thin film technology with each filter element 28 fabricated on the same substrate 30 as the lenslet array 18 on an opposite side from the blazed grating 32 of and associated with each lenslet 20. In alternative embodiments, other filter structures such as a Fabry-Perot filter 34 shown in FIG. 4 may be employed. Each Fabry-Perot filter element 36 associated with each lenslet 20 incorporates dual reflecting surfaces 38a and 38b supported in a spacing structure 40 for tuning of the filter element for the desired wavelength. In yet other alternative embodiments, Bragg grating cavities or fixed Fabry-Perot cavities may be employed for the filter elements The exemplary lenslet array for the embodiment described employs 16 lenslets for 16 separate wavelengths. In alternative embodiments an array of 1 to n×n lenslets may be employed with a detector using the order detection and associated filters described.

Figure 5A:
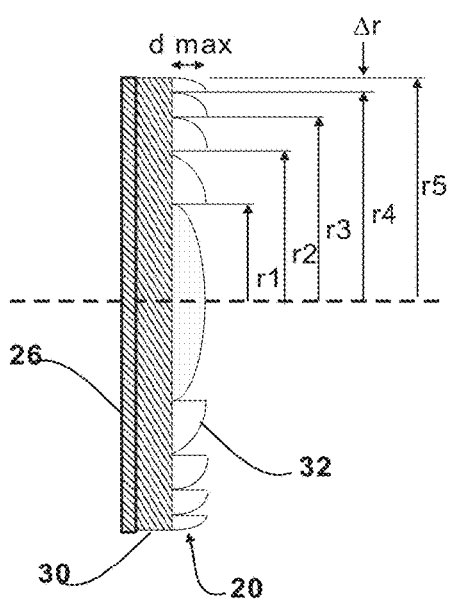
FIGS. 5A and 5B are side and rear views of an example lenslet in the lenslet array.
Figure 5B:
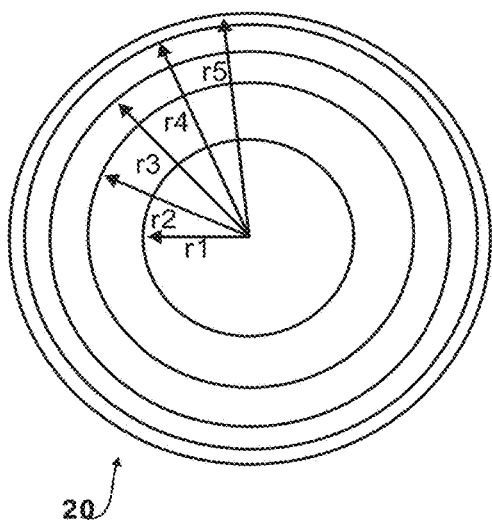

The details of an exemplary lenslet 20 are shown in FIGS. 5A and 5B. The circular blazed grating 32 is fabricated on the substrate 30, for exemplary embodiments using photolithographic process (MEMS or MOEMS), having radii r1-rn with a maximum depth, dmax. as shown in Table 2.

TABLE 2

| | | | | |
|---|---|---|---|---|
| Daimeter of lenslet | D | 3072 | (um) | |
| Radius of lenslet | R | 1536 | (um) | |
| Focal Length | f | 7 | (mm) | |
| f/# | f_num | 2.28 | (num) | |
| First phase coefficient | a | 0.07 | (mm$^-$1) | 1/(2f) |
| Design Wavelength (first order) | lo | 4.35 | (um) | |
| n_total | n | 39 | (num) | f/(8lo(f/#)$^2$) |
| Refractive Index of material | No | 2.78 | | |
| dmax | d | 2.44 | (um) | lo/(No-1) |
| Radius of center zone | r1 | 246.78 | (um) | sqrt(lo/a) |
| | r2 | 349 | (um) | r1 * sqrt(2) |
| | r3 | 427.43 | (um) | r1 * sqrt(3) |
| | r4 | 493.56 | (um) | r1 * sqrt(4) |
| | r5 | 551.82 | (um) | r1 * sqrt(5) |
| | r6 | 604.48 | (um) | r1 * sqrt(6) |
| | r7 | 652.92 | (um) | r1 * sqrt(7) |

TABLE 2-continued

|  |  |  |  |
|---|---|---|---|
|  | r8 | 698 (um) | r1 * sqrt(8) |
|  | r9 | 740.34 (um) | r1 * sqrt(9) |
|  | rn − 1 | 1521.25 (um) | r1 * sqrt(n − 1) |
| Radius to last zone | rn | 1541.14 (um) | r1 * sqrt(n) |
| Delta r min | Drmin | 19.82 (um) | 2 * lo * f/# |

Figure 6:
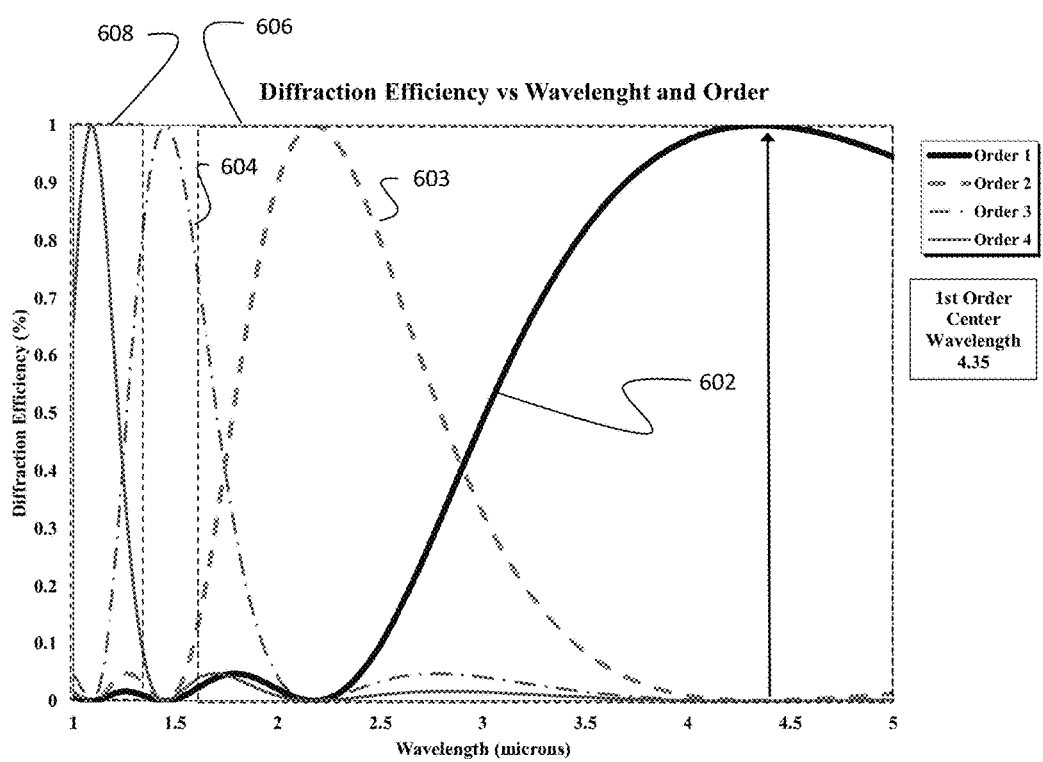
FIG. 6 is a graphical representation of diffraction efficiency as a function of wavelength and order for an example lenslet and order filter.

The embodiment shown in FIG. 5A employs the thin film filter element 28 on the substrate 30 opposite the circular blazed grating 32. For the lenslet 20a as defined in table 1, FIG. 6 demonstrates the diffraction efficiency based on wavelength and order for the lenslet. The $1^{st}$ order, trace 602, has a center wavelength at 4.35 microns while the $3^{rd}$ order, trace 604, has a center wavelength at 1.45 microns. The $2^{nd}$ order, trace 603 is also shown for reference. By providing a bandpass filter element 28a, represented by blocks 606 and 608, with a low cut off at 1.33 microns and a high cutoff at 1.59 microns very high rejection of crosstalk (above 90%) is isolated for transmission to the FPA 22 at the desired detection wavelength corresponding to the $3^{rd}$ order wavelength.

The lenslet array 18 for the embodiments as shown in FIG. 1 is translatable along an optical axis 42 to alter the focal length for tuning of the received wavelengths of radiation at the FPA detector as disclosed in U.S. Pat. No. 7,910,890 having a common assignee with the present application, the disclosure of which is incorporated herein by reference. Order filter 26 employs wavelength characteristics sufficient to accommodate wavelength shift for the variable focal length or, in the case of a Fabry-Perot filter or similar structure, may also be tunable separately or in conjunction with the translation of the lenslet array for a comparable wavelength shift. The filter can also be a fixed spectral bandpass for a lenslet array that is not translated along the optical axis, i.e. for multi-spectral imaging and not hyperspectral imaging.

Figure 7:
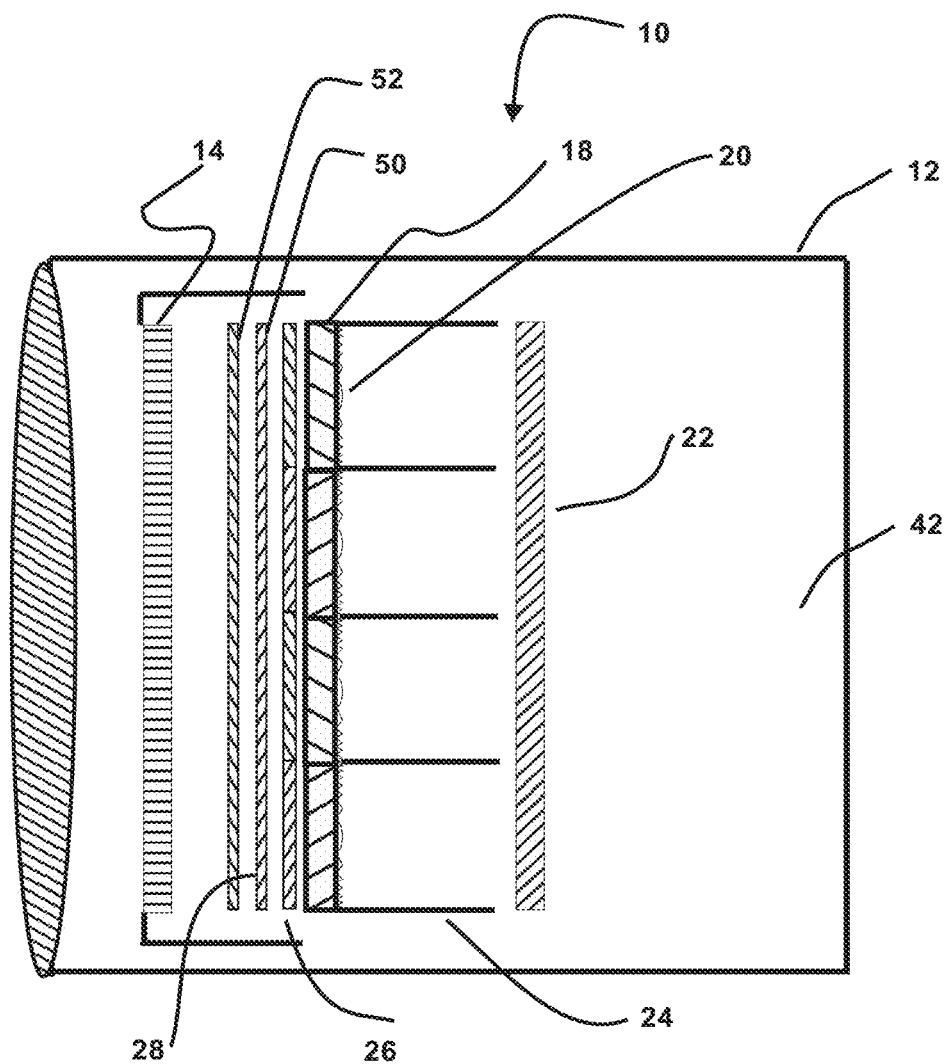
FIG. 7 is a schematic side view of the spectral radiation detector further including a polarizing filter element.
Figure 8:
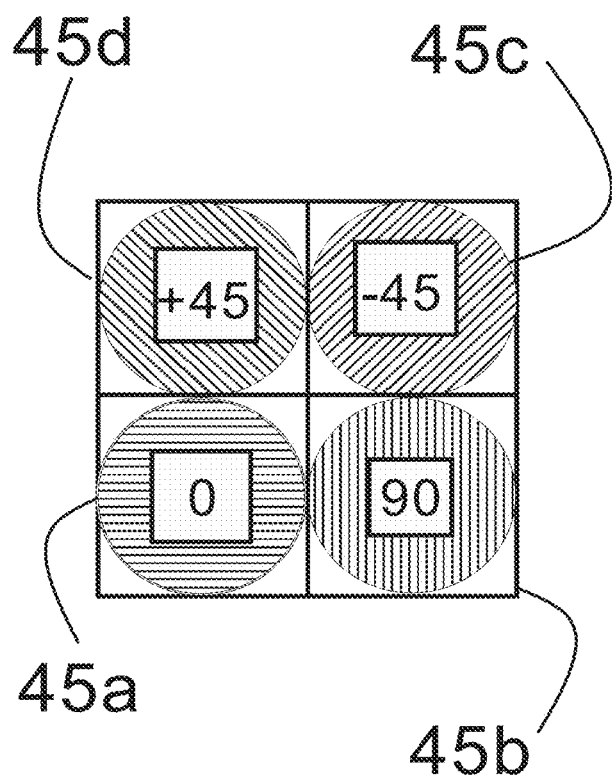
FIG. 8 is a front view of a polarizing filter quad.
Figures 9, 10, 11:
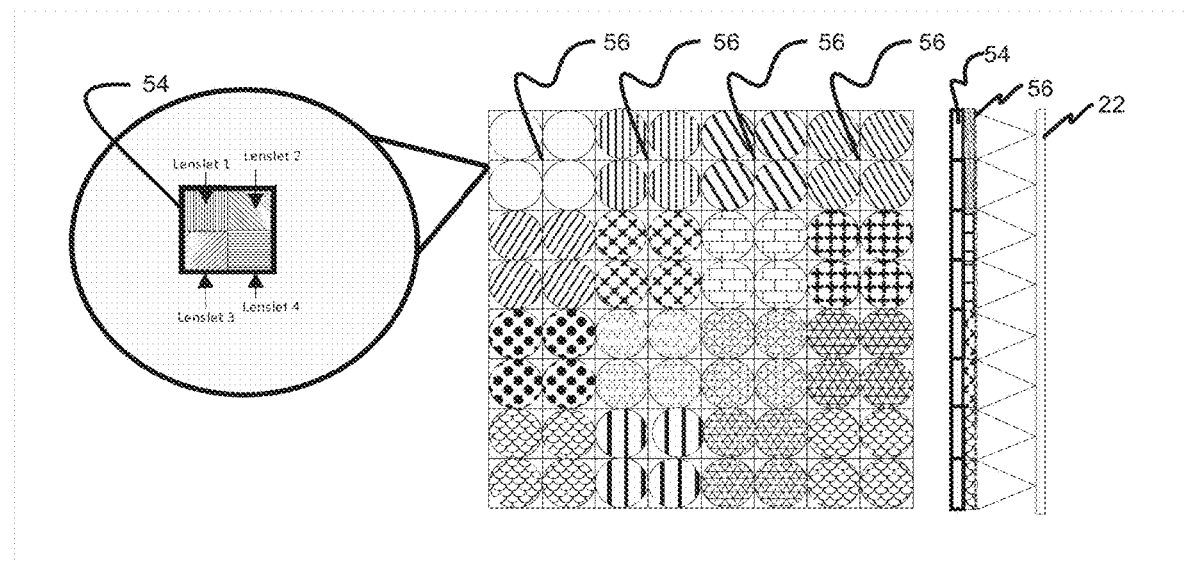
FIGS. 9 and 10 are front and side views of a lenslet array demonstrating lenslet quads associated with polarizing filter quads.
FIG. 11 is a blow up view of polarizing filter quads associated with lenslet quads of the array of FIG. 9.
Figure 12:
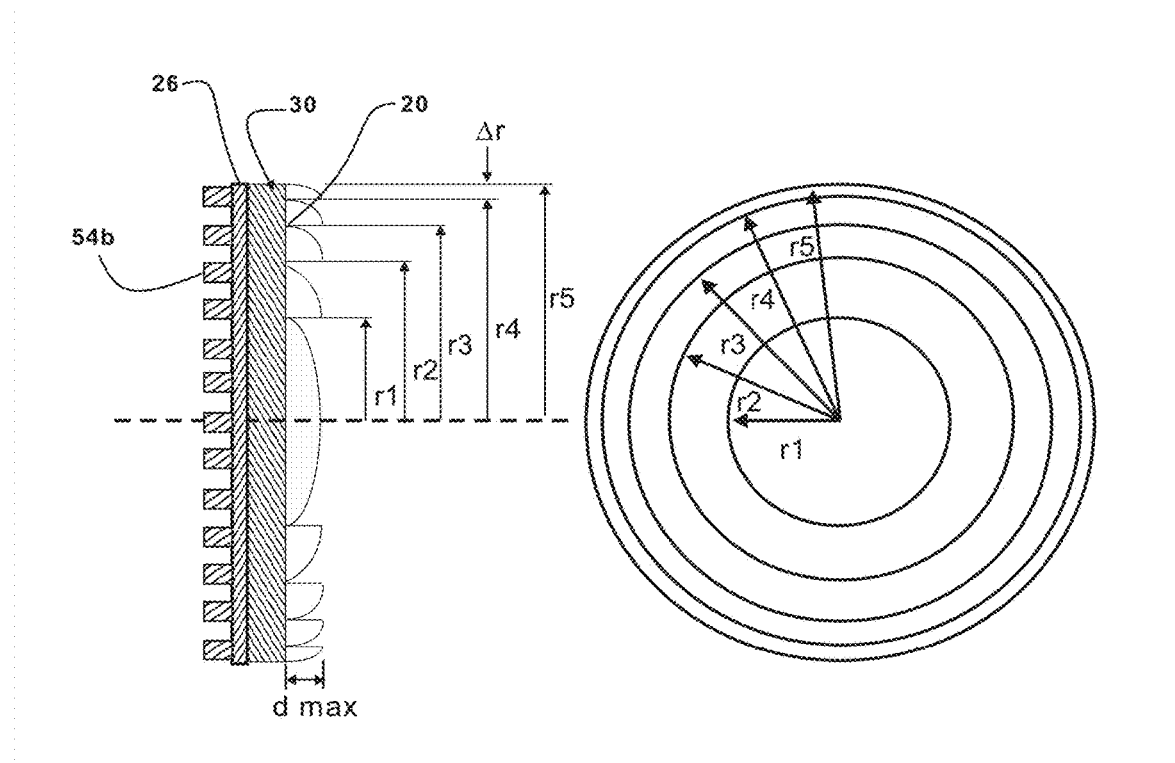
FIG. 12 is a side view of an example single lenslet with the order filter and polarizing filter integrated in thin film technology on the same substrate.

The embodiments disclosed in FIG. 1 and described above divide an aperture associated with the collimating lens into images of different wavelengths associated with each lenslet in the lenslet array. Additional discrimination capability is created by the addition of a polarizing filter array 50 as shown in FIG. 7. Radiation entering the spectral radiation detector 10 is collimated by the collimating lens 16 and passed through a broadband filter 52. The order filter array 26, as previously described, passes radiation to the lenslet array 18 at a desired order wavelength for detection by the FPA 22. Polarizing filter array 50 provides up to four filter units as a filter quad having a polarized filter element 54a, 54b, 54c and 54d each associated with one of a set of four lenslets as shown in FIG. 8. For the embodiment shown in FIGS. 9 and 10, the 16 lenslets of FIG. 2 are replaced by 64 lenslets grouped in lens quads 56 with each lenslet in the quad blazed to provide radiation to the focal plane at the FPA at nth order for a wavelength, λ. The wavelengths defined in Table 1 would be examples of the wavelengths for the 16 quads 54 of the exemplary embodiment of FIG. 9. As shown in FIG. 11, the filter elements 54a-54d in each quad may be polarization film or pattern, for example a wire grid, and may be integrated on the same substrate as the lenslet array as shown in FIG. 12, with or without the thin film filter array, or on a separate substrate that is mechanically mounted in front of or behind the lenslets. The polarizers may be integrated with the order filter on a separate substrate. The array of lenslets for this form of embodiment can be as few as 2×2 or as many as n×n. Additionally, while shown for these embodiments as quads of four polarizing filters providing 0°, 90°, +45° and −45° of polarization, fewer polarizing filters with associated lenslets may be employed and the lenslet array may be An×An where A is the number of selected polarizing angles.

Figure 13A:
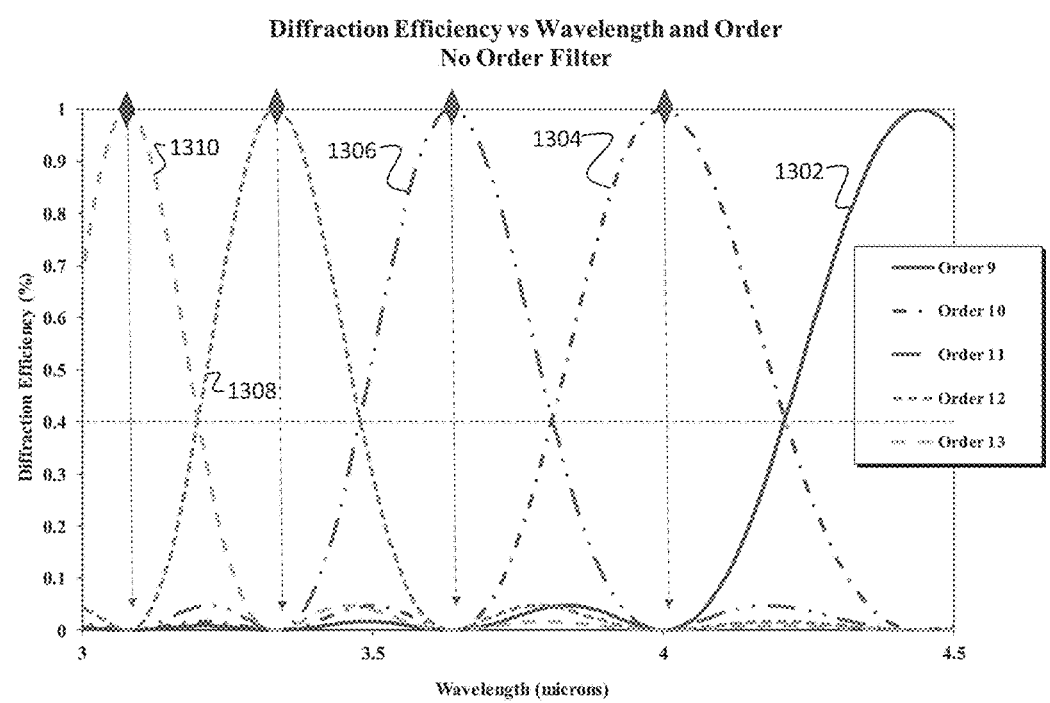
FIGS. 13A-D are graphs of diffraction efficiency vs. wavelength and order with no order filter, a filter blocking order 13, a filter blocking orders 12 and 13, and a filter blocking orders 11, 12 and 13.
Figure 13B:
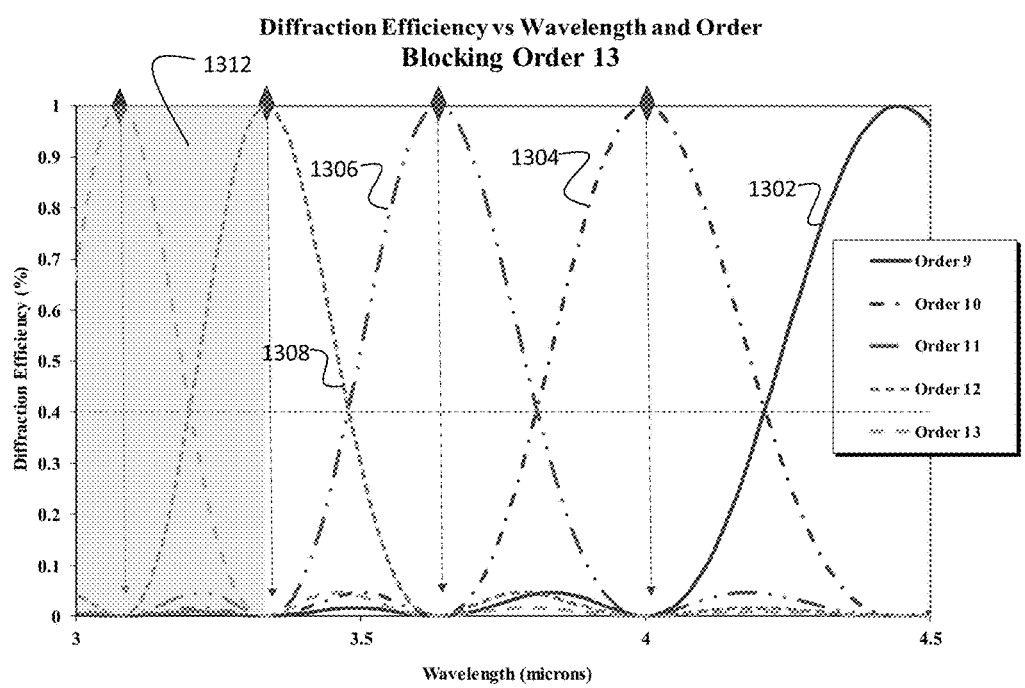
Figure 13C:
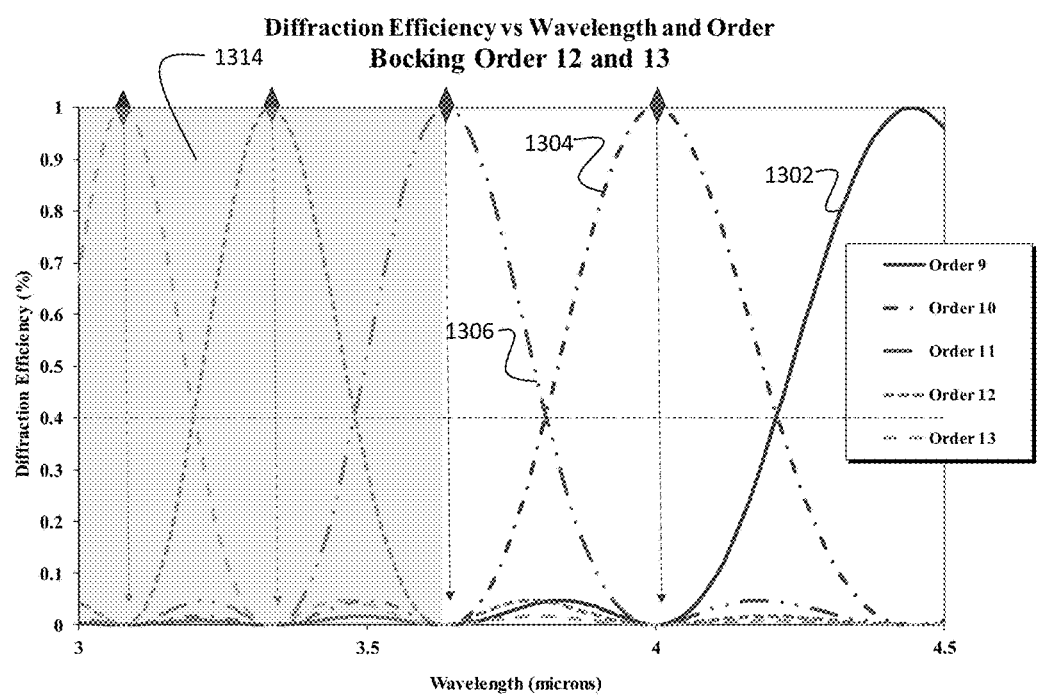
Figure 13D:
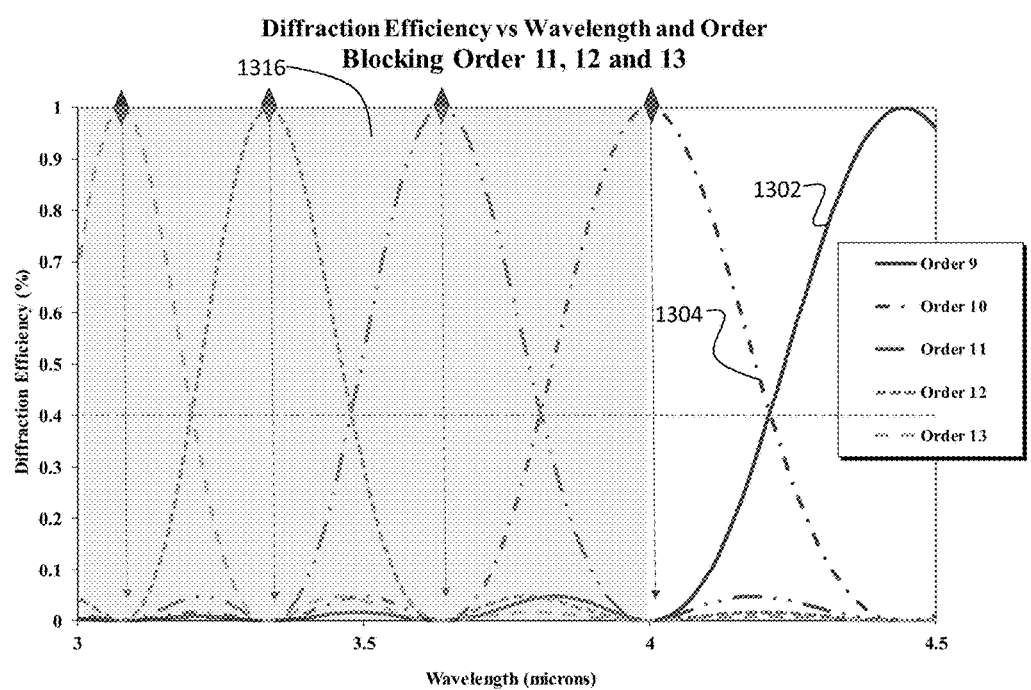

The structure of the lenslet array and FPA may also be employed specifically for gas imaging. FIG. 13A shows the diffraction efficiency for higher orders, order 9 in trace 1302, order 10 in trace 1304, order 11 in trace 1306, order 12 in trace 1308 and order 13 in trace 1310, as a function of wavelength. FIG. 13B is representative of a filter 1312 blocking order 13, FIG. 13C is representative of a filter 1314 blocking orders 12 and 13, and FIG. 13D is representative of a filter 1316 blocking orders 11, 12 and 13. For the example shown in the graphs the diffractive optic is blazed at 40 microns with a focal length of F. The property of a diffractive optic is that all orders will focus at the same focal length. A combination of order filters is employed to a detect gas signal at each pixel in the focal plane array.

Figure 14:
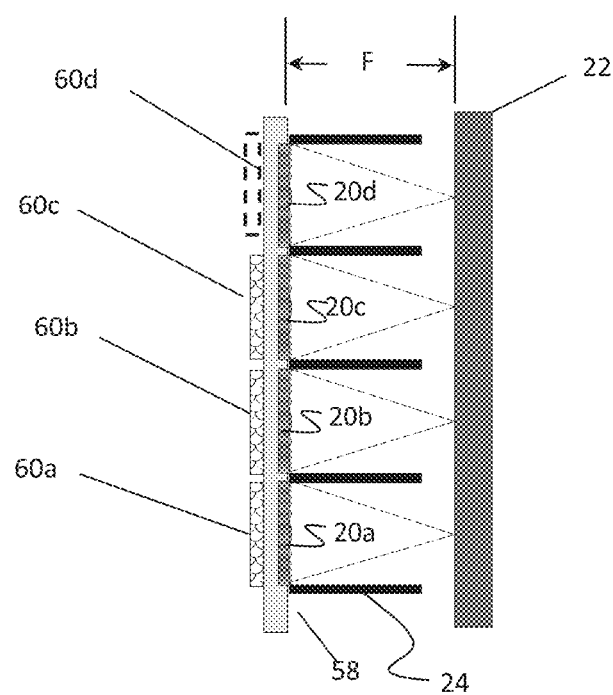
FIG. 14 is a representation of a first embodiment of gas detector optics providing four lenslets each associated with no order filter or order filters for blocking m13, m12 and m13 and m11, m1 and m13.

In a first exemplary embodiment seen in FIG. 14, four diffractive optic lenslets 20a, 20b, 20c and 20d are each associated on a support 58 with different order filters 60a, 60b, 60c and 60d which in the example is a filter passing all the desired orders (or no filter), respectively. Segregated by baffles 24, an array of pixels in FPA 22 receive the radiation from each lenslet and filter combination. The spatial resolution of the gas imaging sensor would be dictated by the size of each pixel, but the overall field of view would be smaller than the full imaging array of FPA 22 by one quarter.

Figure 15:
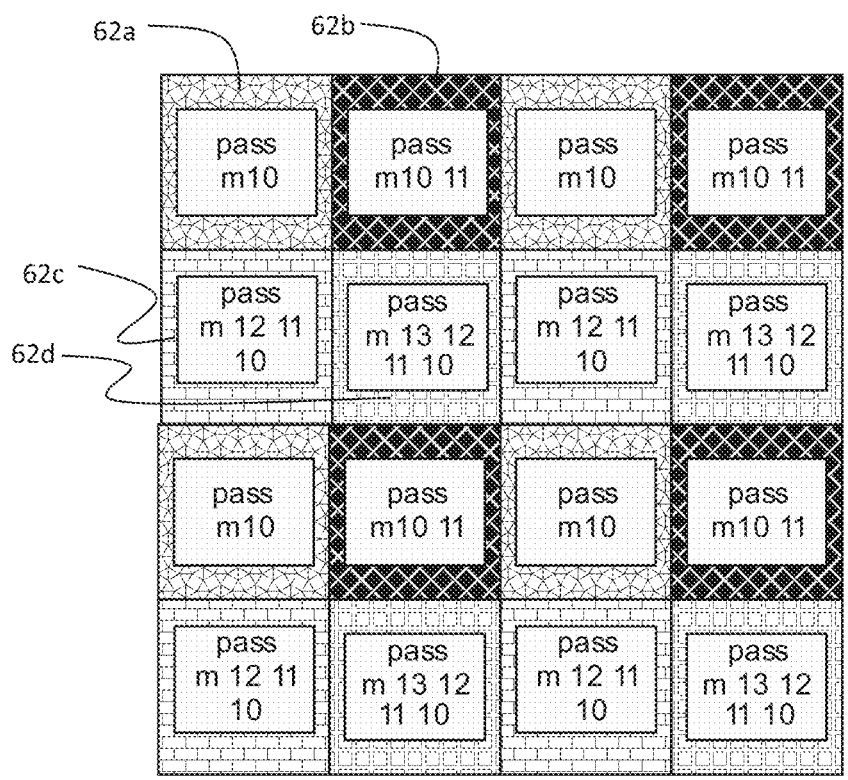
FIG. 15 is a representation of a duplicating array of a 2×2 filter pattern for passing m10; m11 and m10; m12, m11 and m10; and m13, m12, m11 and m10, respectively.
Figure 16:
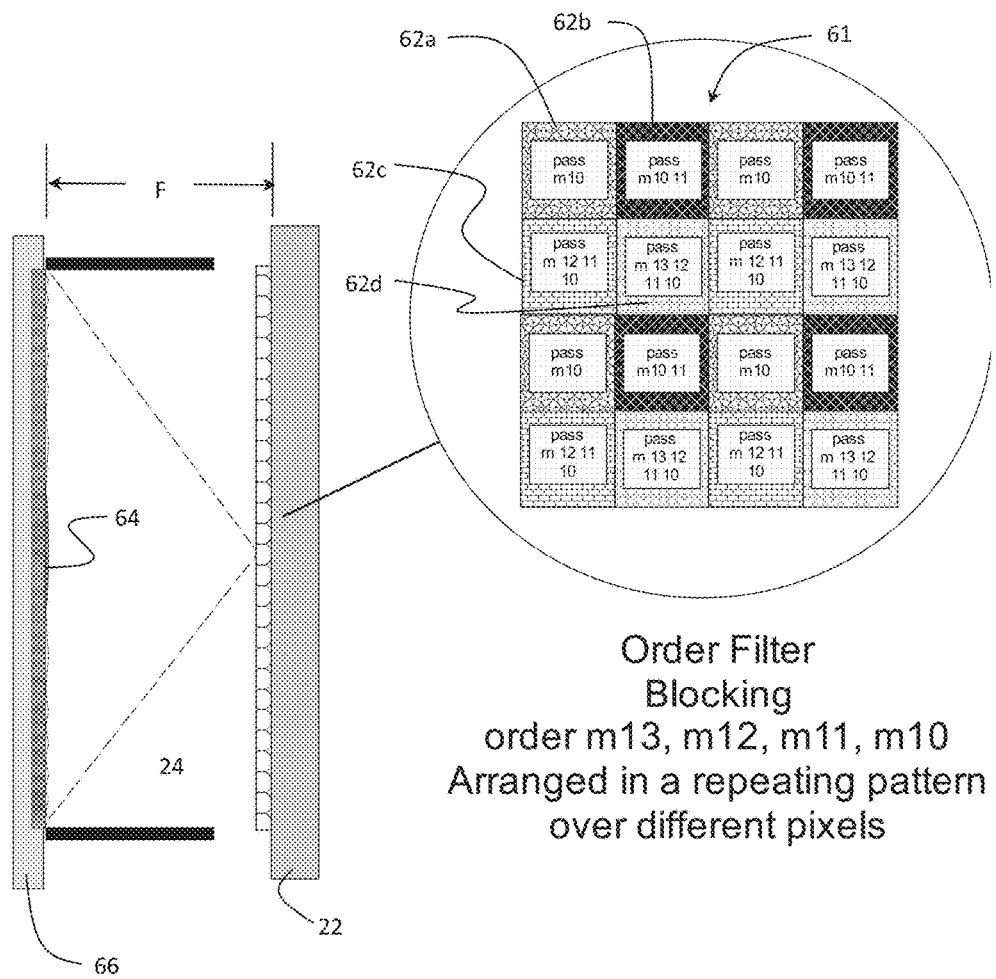
FIG. 16 is a representation of a second embodiment of gas detector optics employing one lens supported over a focal plane array having the repeating array of filters as shown in FIG. 14.

For a second exemplary embodiment, a repeating array 61 of individual order filters 62a passing order 10, 62b passing orders 10 and 11, 62c passing order 10, 11 and 12 and 62d passing orders 10, 11, 12 and 13 (which may be no filter) are patterned for association with individual pixels in the FPA as seen in FIG. 15. This 2×2 filter structure is applied in a repeating pattern on the FPA 22 with a single lens 64 on a support 66 with light baffles 24 directing radiation to the FPA as seen in FIG. 16. Where the image array of the FPA 22 is covered by the single diffractive optical element 64 and thus a larger field of view than the first embodiment, the pixel resolution would be the same but each pixel in the pattern is imaging different wavelengths depending on the order filter.

Figure 17:
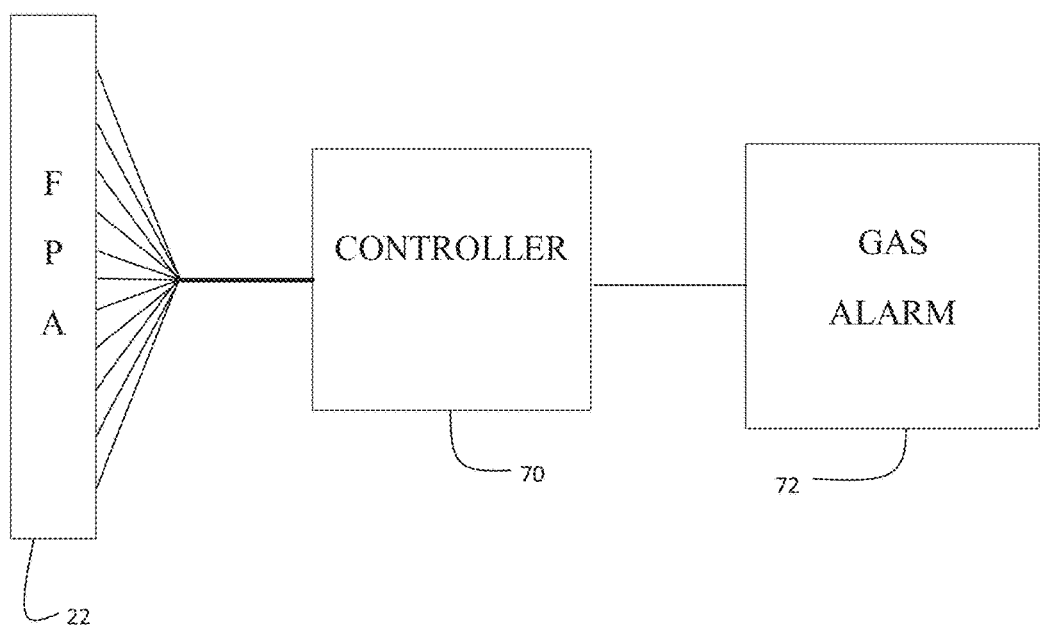
FIG. 17 is a block diagram of a gas detector employing the focal plane array of the detector optics with a controller and gas alarm.
Figure 18:
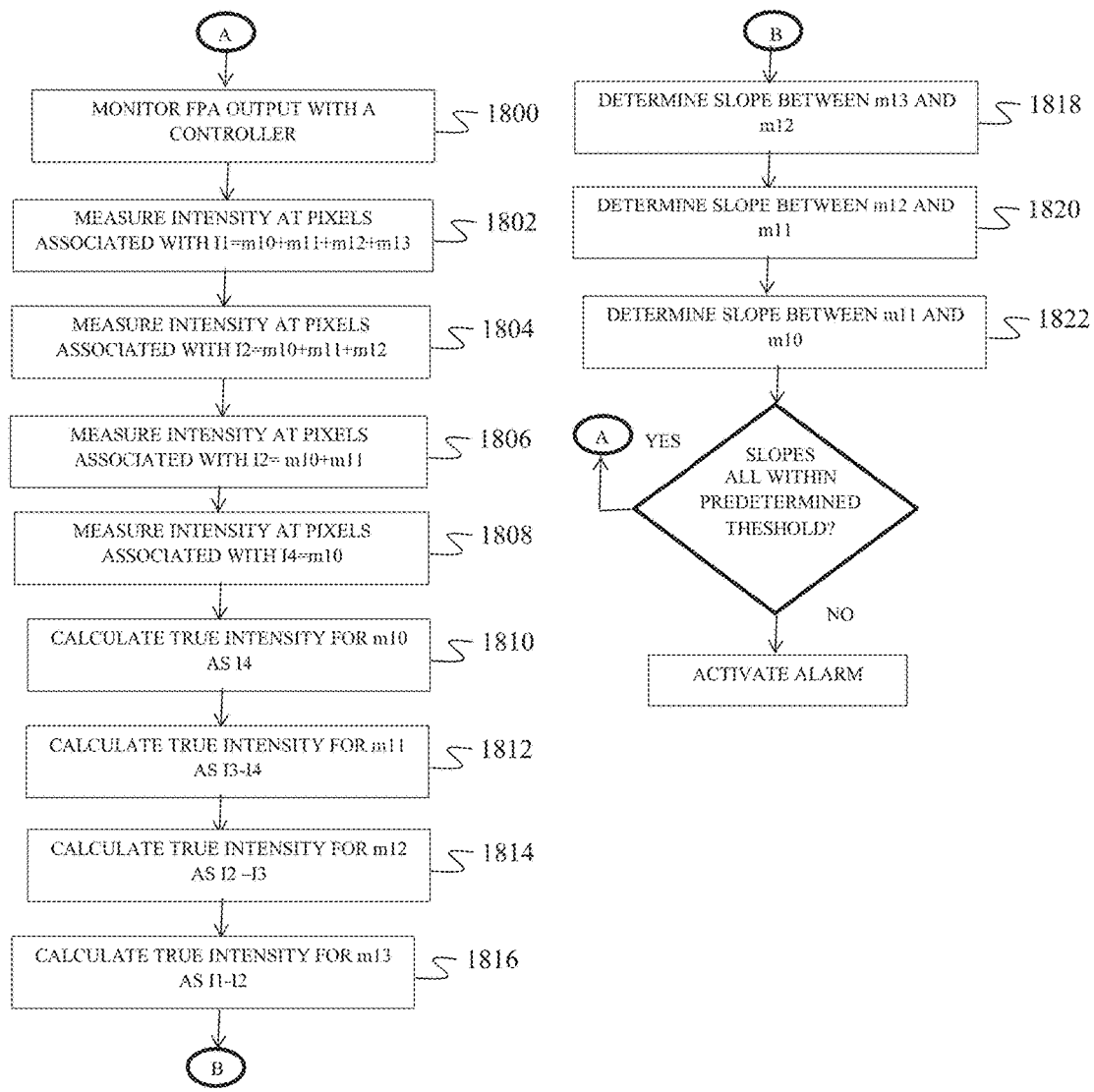
FIG. 18 is a flow chart showing operation of the gas detector of FIG. 17.

For either embodiment, the intensity of the spectral signal for each pixel can be used to determine if there is gas present in that pixel. As seen in FIG. 17, a gas detector 68 may employ a controller 70 adapted to receive outputs from the pixels in the FPA 22 and provided with calculation modules adapted for a determination of gas presence. Upon identification of gas the controller 70 issues an output signal to an annunciator or similar alarm device 72. The controller may employ a standard general purpose microprocessor or a dedicated application specific integrated circuit (ASIC) or field programmable gate array FPGA or similar device. In an exemplary embodiment the calculation modules are employed as shown in FIG. 18 to determine if the signal from a pixel or combination of pixels is associated with a gas in the scene or not. For the first embodiment the signal from each of the set of pixels behind the four diffractive optics is employed, and for second embodiment the four pixels in each 2×2 order filter pattern behind the single diffractive optic are employed. By combining the information detected from the order filter configuration the intensity of each spectral order can be deconvolved where In is the intensity of the nth pixel in the pattern and where mn indicates the higher order spectral signal contributing to the intensity measured by the detector pixel. The outputs of the pixels in the FPA 22 are monitored by the controller 70, step 1800. I1 is measured as I1=m10+m11+m12+m13 (no order filter for this pixel and all orders contribute to the signal intensity), step 1802. I2 is measured as I2=m10+m11+m12 (order filter blocking order I3 and intensity is the sum of 3 orders), step 1804, I3 is measured as I3=m10+m11 (order filter blocking order I2 and I3 and intensity is the sum of 2 orders). Step 1806. Finally, I4 is measured as I4=m10 (order filter blocking order m11 and m12 and m13 and the intensity is from a single order), step 1808.

To separate the four order spectral signal intensity into the true intensity for each wavelength I4=m10, step 1810, I3-I4=m11, step 1812, I2-I3=m12, step 1814 and I1-I2=m13, step 1816.

Figure 19:
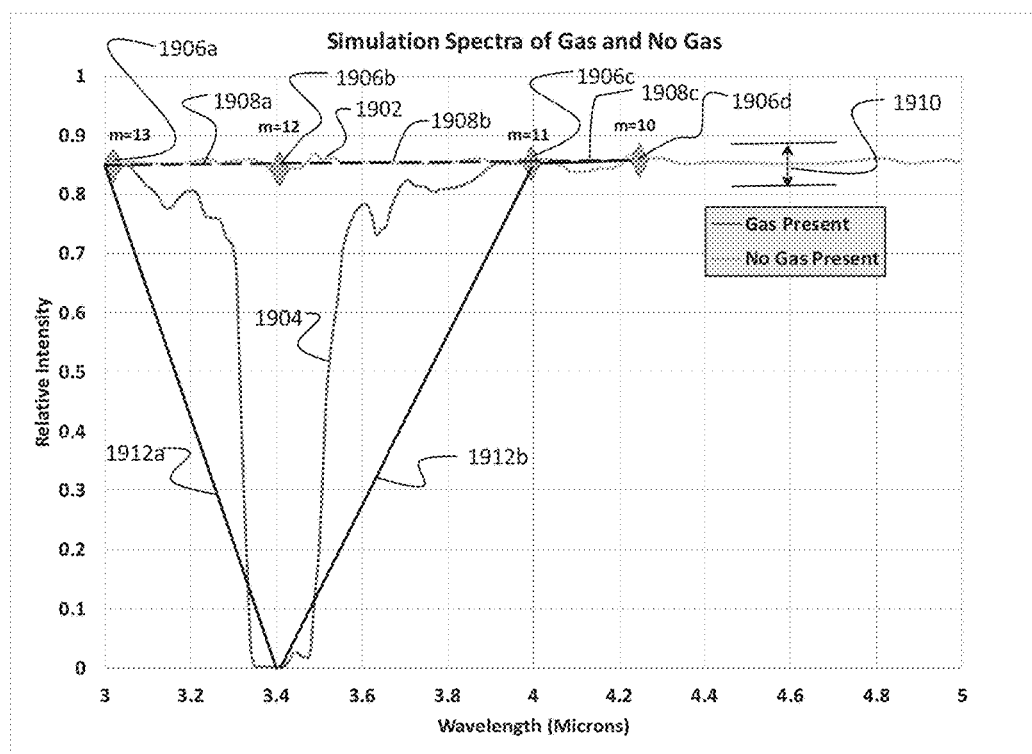
FIG. 19 is a graph of a simulated spectra with and without the presence of a gas of interest.

With the four spectral signatures separated as shown then the relationship between the wavelength signals intensity can be used to determine if gas is present in each pixel. This process is repeated for all the pixels in the image, Shown in FIG. 19 is a simulated spectra of a background ambient scene, trace 1902, superimposed with the transmission spectra of butane gas, trace 1904. The values calculated for I1 to I4 are indicated by the diamonds 1906a for order m=13, 1906b for order m=12, 1906c for order m=11 and 1906d for order m=10 without gas present are the intensity measure with the diffractive optic and order filters which have been separated as shown above. With gas present, for order m=12 diamond 1906b' is displaced. As seen in FIG. 19, the slope of line 1908a between diamond 1906a and 1906b, step slope of line 1908b between diamonds 1906b and 1906c, slope of line 1908c between diamonds 1906c and 1906d have comparable slopes below a predetermined threshold 1910 indicating no gas is present in the scene at the associated pixel. However, if the slope of any of the lines between the order values exceeds the predetermined threshold (the increased slopes of line 1912a between diamonds 1906a and 1906b' and line 1912b between diamonds 1906b' and 1906c) then the gas is present. Returning to FIG. 18, the slopes between the four data points are determined; determine slope between m13 and m12, step 1818, determine slope between m12 and m11, step 1820, determine slope between m11 and m10, step 1822. If the slopes are all with the predetermined threshold, step 1824, then monitoring continues. If any slope is outside the threshold then the gas present signal is activated in the alarm 72, step 1826.

In alternative embodiments, more than four order filters may be employed, or translation of the lenslet or lenslet array with the order filters may be accomplished along the optic axis as previously described to sample more spectral data points to give higher spectral resolution.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A gas detector comprising:
    a plurality of lenslets for a set of wavelengths, each lenslet with a circular blazed grating for diffraction of radiation to a focal plane;
    a detector at the focal plane receiving radiation passing through the at least one lenslet for detection at a predetermined diffraction order; and,
    a plurality of order filters associated with the plurality of lenslets to pass radiation at wavelengths corresponding to the predetermined diffraction order to the detector, each filter blocking a selected set of higher orders wherein the plurality of order filters is equal in number to the plurality of lenslets, each order filter associated with one lenslet of the plurality of lenslets to pass radiation at wavelengths corresponding to the predetermined order to associated pixels of the detector;
    a controller receiving input from associated pixels associated for each of the plurality of order filters in the detector and having
        a module adapted to deconvolve intensity, In, at the associated pixels in the detector for each of the plurality of order filters where n equals the number of order filters and
        a second module to determine a presence of gas by a slope between true intensities at wavelengths of any two of the order filters exceeding a threshold.

2. The gas detector as defined in claim 1 wherein the plurality of lenslets comprises four lenslets, each associated with a plurality of pixels in the detector.

3. The gas detector as defined in claim 1 wherein the at least one lenslet comprises a lens for diffraction of radiation to the focal plane, and
    wherein the plurality of order filters comprises a repeated pattern of an array of order filters, each order filter in the array associated with one pixel of the detector.

4. The gas detector as defined in claim 3 wherein the array of order filters comprises a 2×2 array.

5. The gas detector as defined in claim 1 wherein the plurality of order filters comprise an first filter blocking order m13, a second filter blocking order m12 and m13, a third filter blocking order m11, m12 and m13 and a fourth filter passing order m10, m11, m12 and m13.

\* \* \* \* \*